(12) United States Patent
Chae

(10) Patent No.: US 11,429,822 B2
(45) Date of Patent: Aug. 30, 2022

(54) FABRIC IDENTIFYING METHOD, APPARATUS, AND SYSTEM

(71) Applicant: LG Electronics Inc., Seoul (KR)

(72) Inventor: Yeon Kyung Chae, Incheon (KR)

(73) Assignee: LG Electronics Inc., Seoul (KR)

( * ) Notice: Subject to any disclaimer, the term of this patent is extended or adjusted under 35 U.S.C. 154(b) by 424 days.

(21) Appl. No.: 16/599,960

(22) Filed: Oct. 11, 2019

(65) Prior Publication Data
US 2020/0042822 A1  Feb. 6, 2020

(30) Foreign Application Priority Data
Aug. 21, 2019  (KR) .......................... 10-2019-0102524

(51) Int. Cl.
G06K 9/62  (2022.01)
G01N 22/00  (2006.01)
G01N 33/36  (2006.01)
G01N 21/25  (2006.01)

(52) U.S. Cl.
CPC ............. *G06K 9/627* (2013.01); *G01N 21/25* (2013.01); *G01N 22/00* (2013.01); *G01N 33/367* (2013.01); *G06K 9/6256* (2013.01)

(58) Field of Classification Search
None
See application file for complete search history.

(56) References Cited

U.S. PATENT DOCUMENTS

2021/0214874 A1*  7/2021  Iancu .................... D06F 34/18

FOREIGN PATENT DOCUMENTS

| KR | 1020060008542 | 1/2006 |
| KR | 1020130135016 | 12/2013 |

\* cited by examiner

*Primary Examiner* — Leon Flores
(74) *Attorney, Agent, or Firm* — Fish & Richardson P.C.

(57) ABSTRACT

Disclosed is a fabric identifying system including a fabric identifying apparatus for identifying the type of a fabric of clothing and a server. The fabric identifying apparatus includes an image camera for obtaining image information on a fabric structure of clothing, a fabric identifier for performing a function of identifying the type of the fabric based on the fabric structure of the image information. The server includes an artificial intelligence model learner for generating a fabric type identifying engine for learning the fabric structure of the image information of the received clothing through a deep neural network, the server is configured to transmit the learned fabric type identifying engine to the fabric identifying apparatus. According to the present disclosure, it is possible to identify the type of the fabric of the clothing by using the artificial intelligence (AI), the artificial intelligence based screen recognition technology, and the 5G network.

18 Claims, 8 Drawing Sheets

FIG. 6A

| Main | Sub |
|------|-----|
| JEAN | JEAN |
| FUR | FUR |
|  | MINK |
|  | ANGORA |
| SILK | SILK |
| WOOL | 100% |
|  | WOOL BLEND |

FIG. 6B

| Address | 0 | 1 | 2 | 3 | 4 | 5 | 6 | 7 |
|---------|---|---|---|---|---|---|---|---|
| Desc. | Checksum | Data1 (Main Category) | | | Data2 (Sub Category) | | | |

FABRIC IDENTIFYING METHOD, APPARATUS, AND SYSTEM

CROSS-REFERENCE TO RELATED APPLICATION

This application claims benefit of priority to Korean Patent Application No. 10-2019-0102524, filed on Aug. 21, 2019, the entire disclosure of which is incorporated herein by reference.

BACKGROUND

1. Technical Field

The present disclosure relates to a method, an apparatus, and a system for identifying a fabric of clothing, and more particularly, to a fabric identifying method, apparatus, and system based on a sensor or artificial intelligence.

2. Description of Related Art

Conventionally, when using clothing-related home appliances such as a washing machine, a clothing manager and a dryer, a user has manually selected a washing/drying function, thereby damaging a fabric by not recognizing the clothing such as wool or fur requiring precaution in advance.

In the related art, a washing apparatus discloses a structure that may perform automatic washing by obtaining information on each clothing that is put into a drum by using a non-contact method, and may accurately recognize each clothing and also prevent water permeation into a RF reader unit. However, the washing apparatus including the RF reader unit for obtaining the RFID tag information of the clothing is capable of automatic washing of the obtained clothing information, but since the washing apparatus attaches the RF reader around the opening of the washing apparatus to obtain the clothing information, there are drawbacks in that it may not be applied to various products and applied only to a specific product group line, and it is also difficult to utilize it if the tag of the clothing is damaged by frequent washing.

In another example of the related art, an apparatus for recognizing a material of an object includes an image camera for capturing a spatial image including various objects existing in a space, an exploration radar for irradiating an incident wave to the objects to receive spatial radar information including a surface reflection wave of the respective surfaces of the objects and the respective inner reflection waves returned from the inside of the objects, an information storage for storing respective reference physical property information corresponding to the material of the objects, and a material recognition processor for recognizing material information of the respective objects by using the reference physical property information of the information storage, the spatial image provided by the image camera, and the spatial radar information provided by the exploration radar. However, since the apparatus for recognizing the material of the object is an apparatus for identifying the material information by the reflection wave information of the exploration radar and inferring the location information of the image with the image information, and may identify the material information only when the reflection wave information of the radar should be present, it has been difficult to confirm the material only by the image information.

SUMMARY OF THE DISCLOSURE

An object of an embodiment of the present disclosure is to minimize the damage of the clothing by identifying a type of the fabric of the clothing without user's interrupt because the material of the clothing may be damaged by not recognizing the fabric requiring precaution in advance by a user manually operating a product when using a clothing-related home appliance.

Another object of an embodiment of the present disclosure is to provide a fabric type matching technology of effectively performing the special clothing function previously provided in a clothing-related home appliance in order to produce a smart clothing-related home appliance.

Still another object of an embodiment of the present disclosure is to perform various functions of the linked device through securing the fabric of the goods with the image information.

The present disclosure is not limited to what has been described above, and other aspects and advantages of the present disclosure will be understood by the following description and become apparent from the embodiments of the present disclosure. Furthermore, it will be understood that aspects and advantages of the present disclosure may be achieved by the means set forth in claims and combinations thereof.

A fabric identifying method, apparatus, and system according to an embodiment of the present disclosure for achieving the objects may transmit fabric information to a clothing-related home appliance by identifying the type of a fabric of clothing based on an AI technology.

Specifically, a fabric identifying method may include obtaining image information on a fabric structure of clothing, applying data on the fabric structure of the image information to a learned artificial intelligence model in order to identify the type of the fabric of the clothing, outputting the information on the type of the fabric from the learned artificial intelligence model, and transmitting information on the identified type of the fabric to a clothing-related home appliance.

A fabric identifying apparatus according to an embodiment of the present disclosure may include an image camera for obtaining image information on a fabric structure of clothing, a fabric identifier for identifying and outputting the type of the fabric through a learned artificial intelligence model based on the fabric structure of the image information, and a communicator for transmitting the information on the identified type of the fabric to a clothing-related home appliance.

A fabric identifying system according to an embodiment of the present disclosure may include a fabric identifying apparatus for identifying the type of a fabric of clothing and a server, and the fabric identifying apparatus may include an image camera for obtaining image information on a fabric structure of clothing, a fabric identifier for identifying and outputting the type of the fabric based on the fabric structure of the image information, and a communicator for transmitting the image information on the fabric structure of the clothing to a server, and the server may include an artificial intelligence model learner for generating a fabric type identifying engine for learning the received image information on the fabric structure of the clothing through a deep neural network, the server may be configured to transmit the learned fabric type identifying engine that has learned through the artificial intelligence model learner to the fabric identifying apparatus, the fabric identifier may be configured to identify the type of the fabric of the clothing through the learned fabric type identifying engine received from the server, and the communicator may be configured to transmit the information on the type of the fabric identified by the fabric identifier to a clothing-related home appliance.

In addition, other methods, other systems, and a computer program for executing the method for implementing the present disclosure may be further provided.

Other aspects, features, and advantages other than those described above will become apparent from the following drawings, claims, and detailed description of the present disclosure.

According to an embodiment of the present disclosure, it is possible to automatically provide the fabric information of clothing to the user by using the artificial intelligence (AI), the AI-based screen recognition technology, and the 5G network.

According to an embodiment of the present disclosure, it is possible to provide the function of notifying the user of the fabric requiring precaution, which is damaged when washed or dried by using the clothing-related home appliance, thereby providing user convenience and reliability of use.

According to an embodiment of the present disclosure, it is possible to receive the fabric information from various product functions that are already provided in the clothing-related home appliance but do not know well and not use, thereby providing the optimal course in the clothing-related home appliance without user intervention.

According to an embodiment of the present disclosure, it is possible to provide the fabric identifying apparatus in the form of detachable/attachable accessory when there has a previously purchased home appliance, thereby using in interlock with the existing home appliance without having to purchase a new product.

According to an embodiment of the present disclosure, it is possible to record the fabric information owned by the user through the data storing apparatus such as a cloud server, confirm the preference function of the user by using it for the product, and provide the optimal course in the clothing-related home appliance.

The effects of the present disclosure are not limited to those mentioned above, and other effects not mentioned may be clearly understood by those skilled in the art from the following description.

BRIEF DESCRIPTION OF THE DRAWINGS

FIG. 6A is an exemplary diagram of a category display on the type of the fabric to be communicated in the fabric identifying apparatus according to an embodiment of the present disclosure.

FIG. 6B is an exemplary diagram of a portion of a protocol on the type of the fabric to be communicated in the fabric identifying apparatus according to an embodiment of the present disclosure.

DETAILED DESCRIPTION

Figure 1:
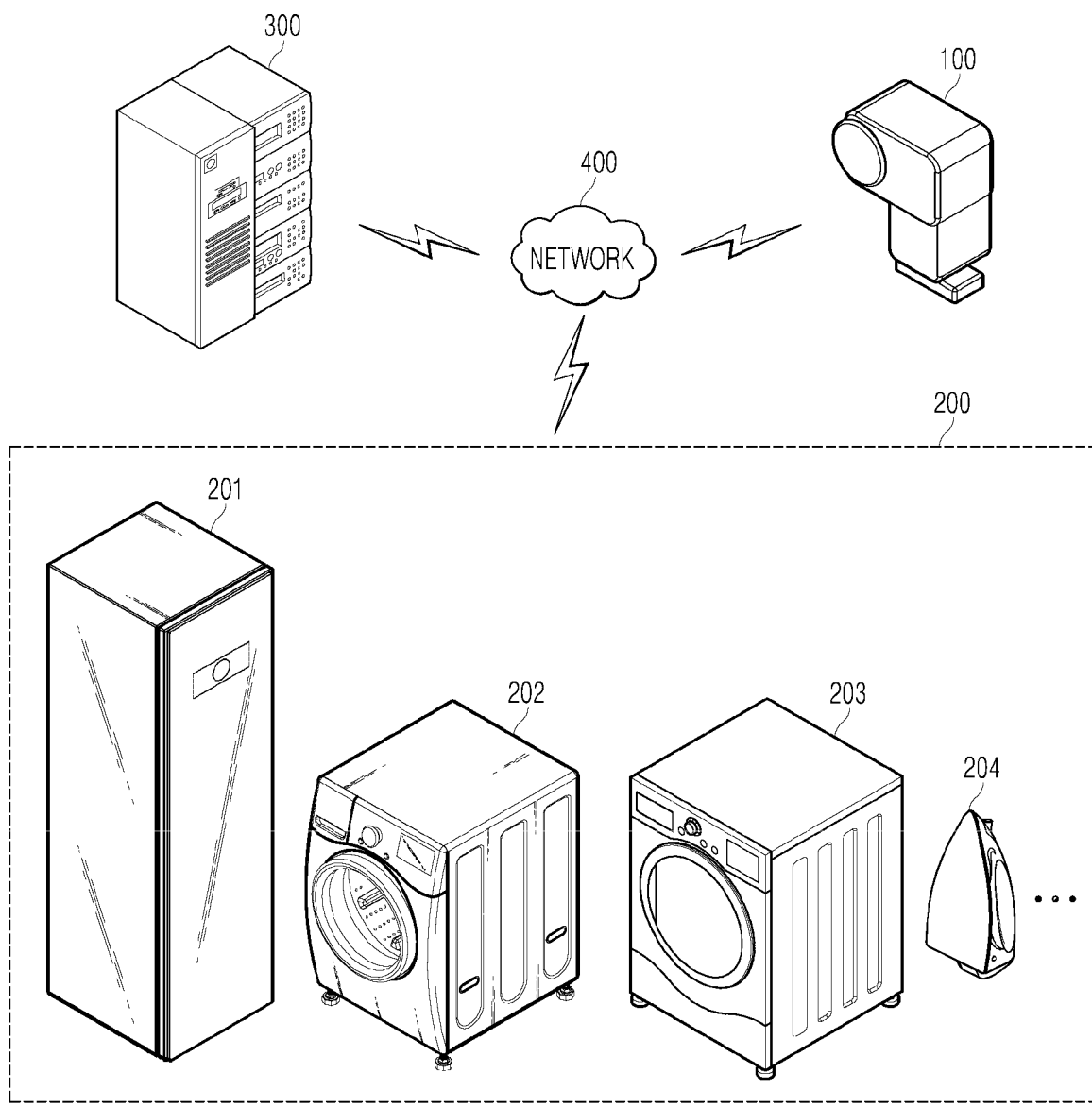
FIG. 1 is an exemplary diagram of a system environment including a fabric identifying apparatus, a clothing-related home appliance, a server, and a network for communicatively connecting them according to an embodiment of the present disclosure.

Advantages and features of the present disclosure and methods for achieving them will become apparent from the descriptions of aspects hereinbelow with reference to the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure. The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "includes," "including," "containing," "has," "having" or other variations thereof are inclusive and therefore specify the presence of conditioned features, integers, steps, operations, elements, and/or components, but do not preclude the presence or addition of one or more other features, integers, steps, operations, elements, components, and/or groups thereof. Furthermore, these terms such as "first," "second," and other numerical terms, are used only to distinguish one element from another element. These terms are generally only used to distinguish one element from another.

Hereinafter, embodiments of the present disclosure will be described in detail with reference to the accompanying drawings. Like reference numerals designate like elements throughout the specification, and overlapping descriptions of the elements will not be provided.

FIG. 1 is an exemplary diagram of a system environment including a fabric identifying apparatus, a clothing-related home appliance, a server, and a network for communicatively connecting them according to an embodiment of the present disclosure.

A fabric identifying apparatus 100 or a fabric identifying system may determine whether there is precise dynamic horizontal defect by using big data, an artificial intelligence (AI) algorithm, and/or a machine learning algorithm in a 5G environment connected for the Internet of Things.

Referring to FIG. 1, a driving environment 1 of the fabric identifying system may include the fabric identifying apparatus 100, a clothing-related home appliance 200, a server 300, and a network 400. The clothing-related home appliance 200 may include a clothing manager 201, a washing machine 202, a dryer 203, and an electric iron 204. The fabric identifying apparatus 100 may include a communicator 134, may transmit sensor data of the fabric identifying apparatus 100 to the server 300 through the wired or wireless network 400, and the server 300 may transmit various fabric information, the learned AI model, and various washing information to the clothing-related home appliance 200 such as the fabric identifying apparatus 100 or the washing machine.

In an embodiment of the present disclosure, the fabric identifying apparatus 100 may communicate with the clothing-related home appliance 200 and the server 300 through the network 400, and perform machine learning such as Deep Learning, and the memory 132 may store data used for machine learning, result data, etc.

The server 300 may be a database server that provides big data required for applying various artificial intelligence algorithms, and data used for operating the fabric identifying apparatus 100. In addition, the server 300 may include a web server or an application server so as to remotely control an operation of the fabric identifying apparatus 100 by using a fabric identifying application or a fabric identifying web browser installed on a user terminal.

Artificial intelligence (AI) is an area of computer engineering science and information technology that studies methods to make computers mimic intelligent human behaviors such as reasoning, learning, self-improving, and the like.

In addition, artificial intelligence does not exist on its own, but is rather directly or indirectly related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed. More specifically, machine learning is a technology that investigates and builds systems, and algorithms for such systems, which are capable of learning, making predictions, and enhancing their own performance on the basis of experiential data. Machine learning algorithms, rather than executing rigidly-set static program commands, may take an approach that builds a specific model based on input data for deriving a prediction or decision.

The network 400 may serve to connect the fabric identifying apparatus 100, the clothing-related home appliance 200, the user terminal 300, and the server 300. The network 400 may include, for example, wired networks such as local area networks (LANs), wide area networks (WANs), metropolitan area networks (MANs), and integrated service digital networks (ISDNs), or wireless networks such as wireless LANs, CDMA, Bluetooth, and satellite communication, but the scope of the present disclosure is not limited thereto. Furthermore, the network 400 may transmit and receive information using short-range communications or long-distance communications. Here, the short-range communications may include Bluetooth, radio frequency identification (RFID), infrared data association (IrDA), ultra-wideband (UWB), ZigBee, and wireless fidelity (Wi-Fi) technology. The long-distance communications may include code division multiple access (CDMA), frequency division multiple access (FDMA), time division multiple access (TDMA), orthogonal frequency division multiple access (OFDMA), and single carrier frequency division multiple access (operation SC-FDMA) technology.

The network 400 may include a connection of network elements such as a hub, a bridge, a router, a switch, and a gateway. The network 400 may include one or more connected networks, for example, a multi-network environment, including a public network such as an internet and a private network such as a safe corporate private network. The access to the network 400 may be provided via one or more wired or wireless access networks. Furthermore, the network 400 may support the Internet of things (IoT) for 5G communication or exchanging and processing information between distributed elements such as objects.

Figure 2:
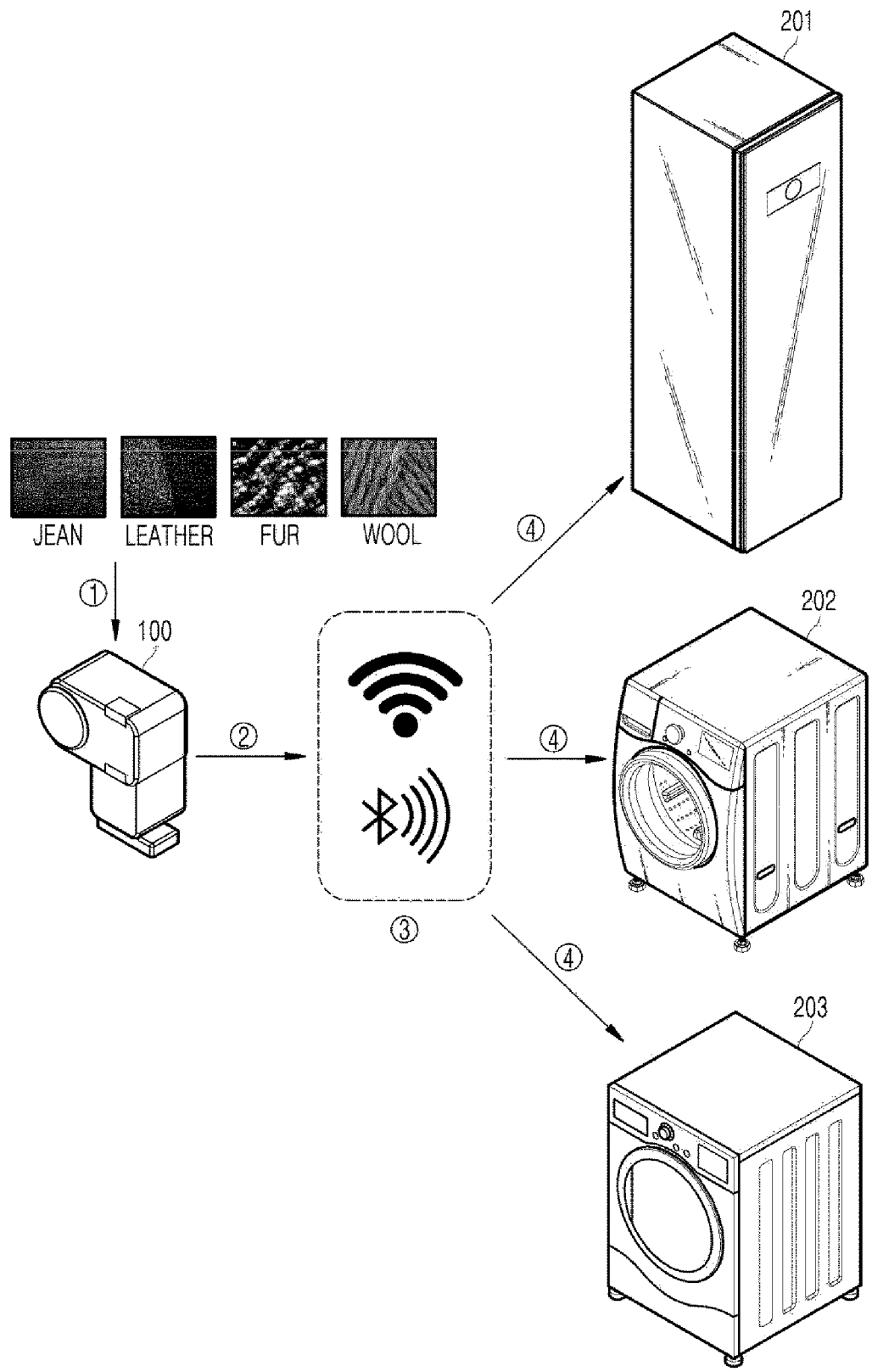
FIG. 2 is an exemplary diagram showing an interlocking process from the fabric identifying apparatus to the clothing-related home appliance with AI based image information according to an embodiment of the present disclosure.

FIG. 2 is an exemplary diagram showing an interlocking process from the fabric identifying apparatus to the clothing-related home appliance with AI based image information according to an embodiment of the present disclosure.

The fabric identifying apparatus 100 identifies the type of the fabric based on at least one data of image information on a fabric structure of the clothing, waveform information from the clothing by a millimeter wave sensor, or information of the near infrared wavelength from the clothing by a near infrared (NIR) spectrometer, and transmits information on the type of the fabric of the clothing to the clothing-related home appliance such as the clothing manager 201, the washing machine 202, and the dryer 203 through Wi-Fi, Bluetooth, IoT, or 5G communication.

In an embodiment of the present disclosure, the fabric identifying apparatus 100 may photograph an image of the clothing by using a magnifying glass camera 112 (①) and identify the fabric and output the result by performing the AI based classification with the feature vector information of the image obtained from the obtained image (②).

The fabric identifying apparatus 100 may be installed in the clothing-related home appliance 200 as an accessory module to interlock between the clothing-related home appliance and the fabric identifying apparatus through Wi-Fi or Bluetooth (③). At this time, the fabric identifying apparatus may be linked in the form of an app program.

The fabric identifying apparatus 100 may convert the classified fabric type result into a control signal to transmit it to the interlocked clothing-related home appliance 200 (④).

The interlocked home appliance 200 may inform the user of the fabric type result based on the classified fabric result and provide washing and drying functions classified according to the fabric. At this time, the fabric information for each of the interlocked home appliances 200 may be confirmed to recommend a special offer course providing for each product, or to provide a notification that there is a risk of damage to the fabric.

Figure 3:
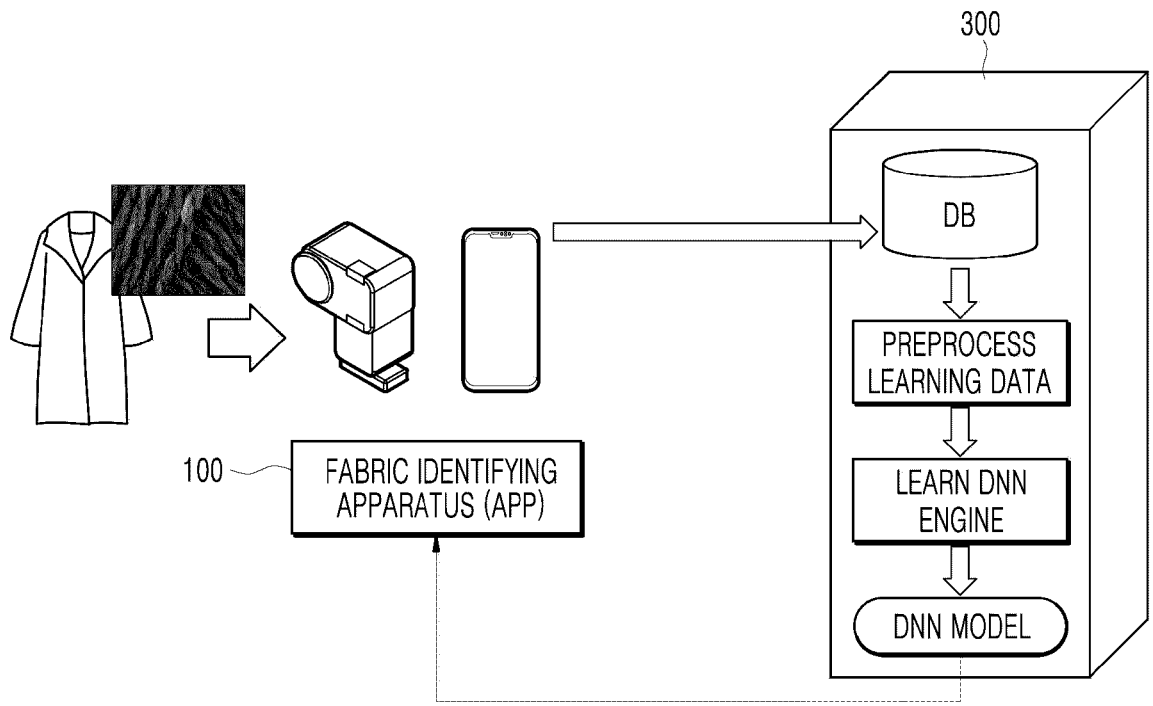
FIG. 3 is an exemplary diagram of a fabric identifying system including the fabric identifying apparatus and the server according to an embodiment of the present disclosure.

FIG. 3 is an exemplary diagram of a fabric identifying system including the fabric identifying apparatus and a server according to an embodiment of the present disclosure.

The fabric identifying apparatus 100 and the server 300 may be equipped with an artificial neural network. In addition, the fabric identifying apparatus 100 may transmit the fabric information of the clothing identified through the learned AI model to the one or more clothing-related home appliances 200 found in response to the operation mode.

The fabric identifying apparatus 100 may use the server 300 for the purpose of learning an AI model that infers (or identifies) the type of the fabric of the clothing. For example, the fabric identifying apparatus 100 may include the AI model learner 124, and directly generate by itself and use the learned AI model for classifying the type of the fabric of the clothing, but the server 300 may include the AI model learner, and also use data in the form of big data collected by the server 300 instead.

The fabric identifying apparatus 100 may use various programs related to an AI algorithm stored in a local area or stored in the server 300. That is, the server 300 may serve to learn the AI model by using data collected together with data collection. The fabric identifying apparatus 100 may classify the type of the fabric of the clothing based on the generated AI model.

The server 300 may receive, from the fabric identifying apparatus 100, at least one of a color, a pattern, or a contour of a specific part of the clothing obtained by the fabric identifying apparatus 100, tag related data, or data on the fabric structure of the specific part. The server 300 may provide the user terminal with the training data necessary for identifying the type of the fabric of the clothing by using the AI algorithm and various programs related to the AI algorithm, for example, an API, a workflow, etc. That is, the server 300 may learn the AI model by using the training data including (i) at least one of a color, a pattern, or a contour of a specific part of the clothing for classifying the type of the fabric, or the tag related data of the clothing, and (ii) the label data on the fabric structure of the specific part. In addition, the server 300 may evaluate the AI model, and update the AI model for better performance even after the evaluation. Here, the fabric identifying apparatus 100 may perform a series of operations performed by the server 300 alone or together with the server 300.

The server 300 may include an AI model learner for generating the learned AI model that has learned the type of the fabric of the collected clothing through a deep neural network (DNN). The AI model learner of the server may be configured to extract the learning data necessary for learning through the deep neural network from the database storing the data necessary for identifying the fabric of the clothing necessary for machine learning or deep learning, to preprocess the learning data in order to increase the accuracy of the learning data, to learn the learning data through the deep neural network (DNN), and to generate the learned AI model.

Data preprocessing refers to removing or modifying learning data to maximally increase the accuracy of source data. In addition, if it contains excessively data whose importance is significantly low, they may also be properly scaled down to change into a form that is easy to manage and use. The data preprocessing includes data refinement, data integration, data transformation, data reduction, etc. The data refinement is to fill missing values, to smooth noisy data, to identify outliers, and to calibrate data inconsistency.

The server 300 may be configured to transmit the learned AI model that has learned through the AI model learner to the fabric identifying apparatus 100. The fabric type classifier 126 of the fabric identifying apparatus 100 may be configured to classify the type of the fabric of the clothing through the learned AI model received from the server.

Figure 4:
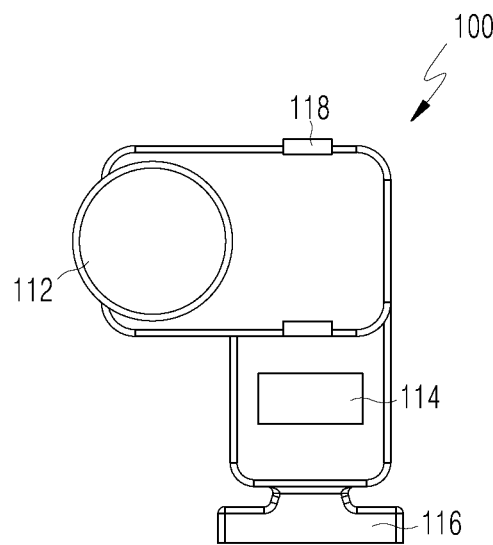
FIG. 4 is a schematic diagram of the fabric identifying apparatus according to an embodiment of the present disclosure.

FIG. 4 is an exemplary diagram of the fabric identifying apparatus according to an embodiment of the present disclosure.

The fabric identifying apparatus 100 may include the magnifying glass 112, a capturing button 114, a cradle 116, and a WiFi and Bluetooth module 118. The magnifying glass 112 for capturing a fabric may be a lens having a high magnification so as to photograph the fabric structure. The magnifying glass 112 may have a magnification of 1 times (1:1) to 100 times (1:100) of the real, but is not limited thereto. In other embodiments, a lens having a high magnification of 100 times or more may be used.

The fabric identifying apparatus 100 may be attached with the WiFi and Bluetooth module 118 for connection with the interlocking home appliance 200, and may include a cradle 116 so as to stand the fabric identifying apparatus 100 upright. The fabric identifying apparatus 100 may include a folding module so as to turn the eyes of the camera for privacy protection.

In another embodiment of the present disclosure, the fabric identifying apparatus 100 may be embedded in the clothing manager 201, the washing machine 202, the dryer 203, etc. The cradle 116 may be integrally integrated in the clothing manager 201, the washing machine 202, the dryer 203, etc., and may use a communicator of the washing machine instead of the WiFi and Bluetooth module 118.

Figure 5:
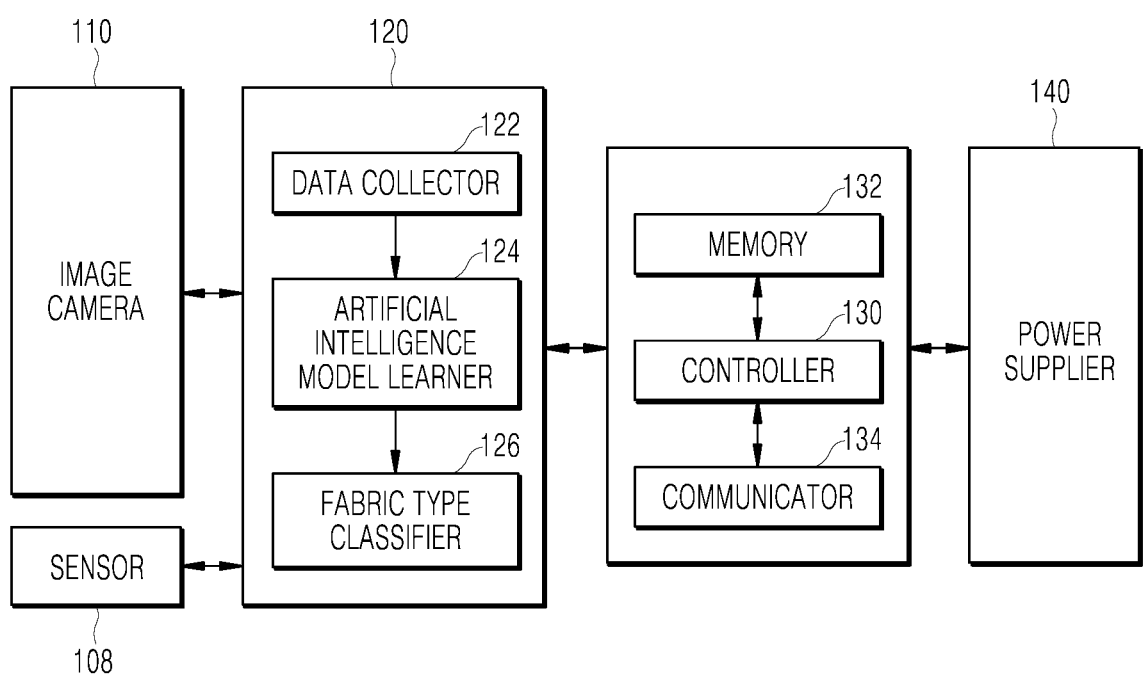
FIG. 5 is a block diagram of the fabric identifying apparatus according to an embodiment of the present disclosure.

FIG. 5 is a block diagram of the fabric identifying apparatus according to an embodiment of the present disclosure.

The fabric identifying apparatus 100 may include an image camera (or vision sensor) 110 for capturing an image of the fabric, and a fabric identifier 120 for identifying the type of the fabric from the captured image. In addition, the fabric identifying apparatus 100 may include the memory 132 capable of storing various data, a communicator 134 capable of communicating with an external device, a power supplier 140 for supplying power to the fabric identifying apparatus 100, and a controller 130 for controlling the image camera 110, the sensor 108, the fabric identifier 120, the memory 132, and the communicator 134 in order to identify the type of the fabric. In addition, the fabric identifying apparatus 100 may include a sensor 108 including a millimeter wave sensor or a near infrared spectrometer (NIR Spectrometer) capable of sensing the fabric structure. The controller 130 may detect the type (material) information of the fabric and generate a control signal having protocol information on the clothing-related home appliance 200 to be communicated with respect to the detected result. The communicator 134 serves to transfer the generated control signal to the interlocked clothing-related home appliance 200.

The millimeter wave (mmWave) sensor is a very useful sensing technology for sensing an object and confirming a range, a speed, and an angle of the object. It is a contactless technology that operates in the 30 GHz to 300 GHz spectrum, and because this technology uses a short wavelength, it may provide accuracy in the range of less than 1 mm and pass through a material such as clothing. The millimeter wave sensor sends a signal by using the wavelength in the millimeter (mm) range, which are regarded as a short wavelength in the electromagnetic spectrum. Actually, a system component such as an antenna necessary for processing a mmWave signal is small in size, and the short wavelength have high resolution. The mmWave system that confirms the distance between the wavelengths may have accuracy of the mm range in 76 to 81 GHz. In an embodiment, the mmWave system may identify the type of the fabric through the AI model learning by using the millimeter wave (mmWave) sensor.

The NIR Spectrometer is based on Texas Instruments' NIRscan™ Nano design and may operate in the wavelength range from 900 nm to 1,700 nm. The NIR Spectrometer may determine the composition of the fiber (for example, blend of 60% cotton and 40% polyester, or 100% wool) by using the near infrared wave. In an embodiment, the NIR Spectrometer may identify the type of the fabric through AI model learning by using the near infrared wave.

The image camera 110 may be captured to obtain an image necessary for identifying the type of the fabric of the clothing, and has a capability capable of capturing a tag of the clothing and a color, a pattern, or a contour of a specific part of the clothing at a specific resolution. The image camera 110 may capture the image of the tag part of the clothing. The tag part of the clothing may be recognized as a character through a character recognition AI algorithm to provide information on the type of the fabric, the brand, and the washing information of the clothing. The character recognition AI algorithm may be configured by using Optical Character Recognition (OCR), a library of TensorFlow, a Python AI library, etc. The recognizing the tag information to obtain information on the type of the fabric may confirm the type of the fabric of the clothing without a function of identifying the type of the fabric, but the tag information may be unreadable as the number of washing increases. Accordingly, when the tag information is readable to be captured by the image camera, the type of the fabric may be determined by the information on the fabric structure of the clothing, or the information on the fabric structure of the clothing by matching the color, the pattern, or the contour of the specific part of the clothing to store it in the memory, or one of the color, the pattern, or the contour of the specific part of the clothing. In addition, the tag information may be used as a label value of the AI model that learns the type of the fabric of the learning data upon supervised learning of the AI model.

The fabric identifier 120 may identify the type of the fabric of the clothing based on at least one of the information on the type of the fabric necessary for learning the AI model from the captured image, at least one of the color, the pattern, or the contour of the specific part of the clothing, the waveform information received from the sensor 108, the near infrared wavelength information, or the tag information of the clothing.

The fabric identifier 120 may learn the AI model based on the data received from the image camera 110 and the sensor 108. For this purpose, the fabric identifier 120 may include a data collector 122 for collecting fabric data on a plurality of fabric structures of the clothing from the image camera 110, the AI model learner 124 for learning by the learning data including data on the plurality of fabric structures and the data that has matched a label of the type of the fabric to data on the plurality of fabric structures, and learning a fabric type identifying engine so as to identify and output the type of the fabric of the clothing, and the fabric type classifier 126 for identifying and outputting the type of the fabric of the clothing through the fabric type identifying engine based on the data on the fabric structure obtained from the image camera 110. The fabric type information of the clothing output from the fabric type classifier 126 may be matched with the data on the fabric structure to be stored in the memory 132, and sent to the clothing-related home appliances 200 through the communicator 134.

In another embodiment of the present disclosure, as described in FIG. 3, the fabric identifier 120 may use the server 300 for the purpose of learning the AI model that infers (or identifies) the type of the fabric of the clothing. The server 300 may receive, from the fabric identifying apparatus 100, at least one of the color, the pattern, or the contour of the specific part of the clothing obtained by the fabric identifying apparatus 100, the tag related data, or the data on the fabric structure of the specific part. The server 300 may be configured to transmit the learned AI model that has learned through the AI model learner to the fabric identifying apparatus 100. The fabric type classifier 126 of the fabric identifying apparatus 100 may be configured to classify the type of the fabric of the clothing through the learned AI model received from the server 300.

The controller 130 of the fabric identifying apparatus 100 may include any type of device capable of processing data, such as a processor, for example, a MCU. Here, 'the processor' may, for example, refer to a data processing device embedded in hardware, which has physically structured circuitry to perform a function represented by codes or instructions contained in a program. As one example of the data processing device embedded in the hardware, a microprocessor, a central processing unit (CPU), a processor core, a multiprocessor, an application-specific integrated circuit (ASIC), a field programmable gate array (FPGA), and the like may be included, but the scope of the present disclosure is not limited thereto.

The communicator 134 of the fabric identifying apparatus 100 may provide a communication interface necessary for providing a transmission/reception signal between the clothing-related home appliance 200 and/or the server 300 in the form of packet data in interlock with the network 400. Furthermore, the communicator 134 may support various kinds of object-to-object intelligent communication (such as Internet of things (IoT), Internet of everything (IoE), and Internet of small things (IoST)), and may support communication such as machine to machine (M2M) communication, vehicle to everything (V2X) communication, and device to device (D2D) communication.

FIG. 6A is an exemplary diagram of a category display related to the type of the fabric to be communicated in the fabric identifying apparatus according to an embodiment of the present disclosure.

The type of the fabric identified by the fabric identifying apparatus from the data on the fabric structure may be configured to have a main classification category and a sub classification category for each category as in FIG. 6A. The main classification may have a synthetic fiber category such as nylon, or polyester in addition to jean, fur, silk, and wool. In the present disclosure, the term 'type of fabric' includes expressing the type of the fabric as a percentage, such as 50% cotton and 50% polyester, or 40% cotton and 60% ramie, for the blend. In another embodiment of the present disclosure, the main classification (sub classification) may have cotton, hemp (linen, ramie, burlap, etc.), wool (surge, muslin, etc.), silk (chiffon, etc.), synthetic fibers (nylon, polyester, rayon, poly-rayon, acrylic, etc.). In another embodiment of the present disclosure, the type of the fabric may be matched with the information on the tag symbol of washing, neutral detergent, dry cleaning, ironing, drying through a predetermined look-up table.

FIG. 6B is an exemplary diagram of a part of a protocol on the type of the fabric to be communicated in the fabric identifying apparatus according to an embodiment of the present disclosure.

The protocol is a communication protocol that smoothly performs the communication for transmitting the result of the type of the fabric identified by the fabric identifier 120 together with the information on the data obtained from the image camera 110 and the sensor 108 to the server 300 and the clothing-related home appliance 200.

A data address 0 checks whether the current data to be communicated is correct. The first to third data addresses include fabric information of a large category (main classification), and the fourth to seventh data addresses include information of sub category (sub classification) to communicate together with the data on the fabric structure. The clothing-related home appliance 200 may share the clothing washing information with a laundry by using a communication protocol.

In another embodiment of the present disclosure, the fabric identifying apparatus 100 may assign clothing identification numbers such as CID0001-1 to CID0001-10000 to the clothing in the order sensed by the image camera 110 or various sensors 108. The clothing identification number may number (CID0001-1) to the number (CID0001) for each fabric identifying apparatus in the order of the clothing captured and identified by the fabric identifying apparatus 100. Since the number of clothing stored and registered in the memory 132 by the fabric identifying apparatus 100 in the home is limited, the fabric identifying apparatus may identify the fabric within the range of the registered clothing once, and perform fabric identification through the fabric identifier 120 to assign a new clothing identification number when it is determined as a unregistered clothing. The first to third protocol addresses in FIG. 6B may be clothing identification numbers registered by the fabric identifying apparatus 100, and the fourth to seventh protocol addresses may be the types of the fabrics corresponding to the clothing identification numbers. When identifying, by the fabric identifier 120, the type of the fabric of the data received from the image camera 110, the fabric identifying apparatus 100 may first search whether there is a previously registered clothing stored in the memory 132 to determine the type of the fabric, and may identify the type of the fabric through the fabric type classifier 126 only when there is no image information of the registered clothing. Since the number of clothing owned in the home is fixed unless a newly purchased one is registered, the type of the fabric needs to be identified only within the database range of the fixed clothing, thereby increasing the accuracy of the identification of the fabric and reducing the identification time by assigning the clothing identification number.

Figure 7A:
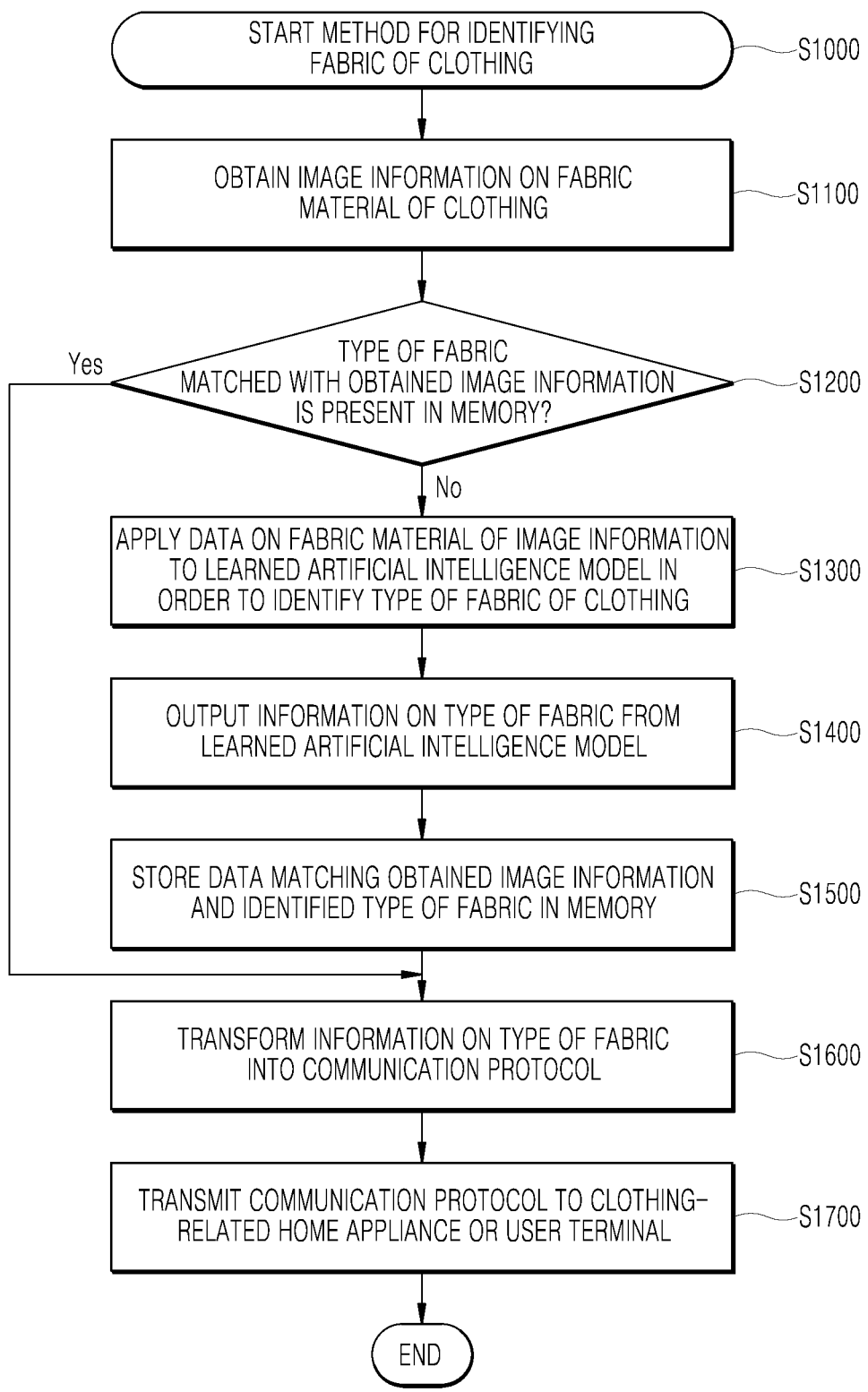
FIG. 7A is a flowchart showing a fabric identifying method according to an embodiment of the present disclosure.

FIG. 7A is a flowchart showing a fabric identifying method according to an embodiment of the present disclosure.

The fabric identifying apparatus 100 may be turned on together when the clothing-related home appliance 200 is turned on, may be turned on by a user setting, and starts a fabric identifying process of the clothing (operation S1000).

The fabric identifying apparatus 100 obtains image information on the fabric structure of the clothing by the image camera 110 (operation S1100). The fabric identifying apparatus 100 may collect data on a full screen by collecting the captured image as it is, resizing the full screen of the image, or cropping a portion of the full screen. When the image of a specific part, for example, a sleeve part, a button part, a neck part, or a lower end part of the clothing having a feature that is distinguished from other clothing is captured through the image camera 110, it may be matched with the image of the fabric structure, thereby identifying more accurate and faster the type of the fabric. In another embodiment, the fabric identifying apparatus may obtain waveform information from the clothing by the millimeter wave sensor, or obtain information of the near infrared wavelength from the clothing by the near infrared (NIR) spectrometer.

The fabric identifier 120 may search whether the type of the fabric matched with the obtained image information is present in the memory (operation S1200). If the type of the fabric matched with the image information obtained in the searching whether the type of the fabric matched with the obtained image information is present in the memory is not present in the memory, applying to the learned AI model (operation S1300), outputting the information on the type of the fabric (operation S1400), storing the data matching the obtained image information and the identified type of the fabric in the memory (operation S1500), transforming into a communication protocol (operation S1600), and transmitting to the clothing-related home appliance (operation S1700) may be performed. If the type of the fabric matched with the obtained image information is present in the memory in the searching whether the type of the fabric matched with the obtained image information is present in the memory, the transforming into the communication protocol without classification through the learned AI model (operation S1600) and the transmitting to the clothing-related home appliance (operation S1700) may be performed.

The fabric identifier 120 may apply the data on the fabric structure of the image information to the learned AI model in order to identify the type of the fabric of the clothing (operation S1300).

The fabric identifier 120 may output the information on the type of the fabric from the learned AI model (operation S1400).

The fabric identifier 120 may store the data matching the obtained image information and the identified type of the fabric in the memory 132 (operation S1500).

The controller 130 may transform the information on the type of the fabric into a communication protocol (operation S1600).

The communicator 134 may transmit the information on the type of the fabric to clothing-related home appliance or a user terminal through the communication protocol (operation S1700).

When it is transmitted to the clothing-related home appliance or the user terminal, the fabric identifying process of the clothing is terminated (operation S1700).

In another embodiment of the present disclosure, a program programmed to execute such a fabric type identifying method may be stored in a computer readable recording medium.

In another embodiment of the present disclosure, the fabric identifying method may be executed in the user terminal in the form of an app. In this case, the obtaining the image information on the fabric structure of the clothing (operation S1100) includes obtaining the image information through a camera of a mobile terminal, and the searching whether the type of the fabric matched with the obtained image information is present in the memory (operation S1200), the applying to the learned AI model (operation S1300), the outputting the information on the type of the fabric (operation S1400), and the storing in the memory (operation S1500) may be performed through a fabric identifying app of the mobile terminal, and the transforming the information on the type of the fabric into the communication protocol (operation S1600) and the communicating the communication protocol with the clothing-related home appliance (operation S1700) may be performed through a communication module of the mobile terminal.

Figure 7B:
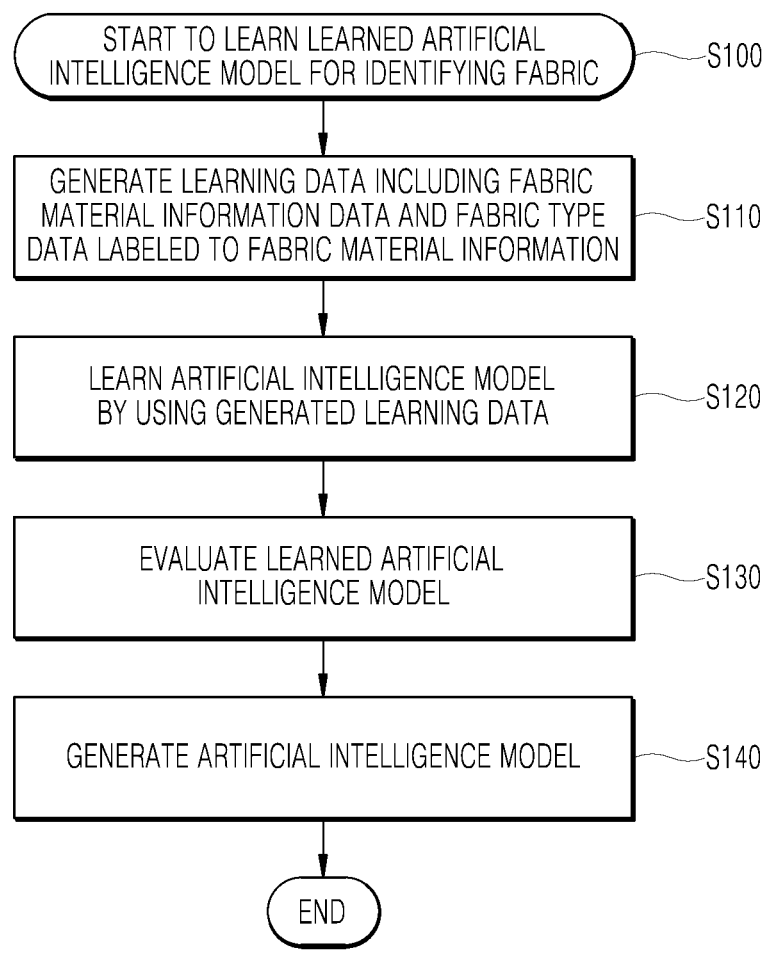
FIG. 7B is a flowchart learning a fabric type identifying engine through an AI model learner according to an embodiment of the present disclosure.

FIG. 7B is a flowchart for learning a fabric type identifying engine through the AI model learner according to an embodiment of the present disclosure.

Referring to FIG. 7B, shown is a process of learning the AI model that identifies the type of the fabric, which may be included in the operation S1300. The AI model learning is started to identify the fabric to be applied in the fabric identifying apparatus 100 (operation S100).

The AI model learning data including fabric data on a plurality of the fabric structure and the data matching a label of the type of the fabric to the plurality of data on the fabric structure may be generated (operation S110). In another embodiment, the data collector 122 may be generated as the AI learning data including at least one of the color, the pattern, or the contour of the specific part of the clothing, the data on the fabric structure of the specific part, or the data matching the label of the type of the fabric to the data on the fabric structure, and test data. The data matching the label of the type of the fabric may generate data matching the information on the type of the fabric of the clothing obtained by recognizing the character of the tag part of the clothing. A ratio of the learning data and the test data may vary according to the amount of data, and may be generally defined as a ratio of 7:3. The collecting and storing the learning data may collect and store at least one of the color, the pattern, or the contour of the specific part of the clothing, or the tag part through the image camera, and collect the captured image through the capture app. The collecting and storing the learning data may collect and store videos and images in the server 300. The AI model learning data may be subjected to data preprocessing and data augmentation in order to obtain accurate learning results.

The AI model, for example, an artificial neural network such as CNN, learns the features of the type of the fabric of the clothing by using the learning data collected through supervised learning (operation S120). The AI model learner 124 may obtain feature vector information of the image from the obtained image, and identify the type of the fabric by performing AI based classification with the feature vector information.

In an embodiment of the present disclosure, a deep learning based screen analyzer may be used, and for example, an AI learning model may be tuned and used based on TensorFlow or MobileNetV1/MobileNetV2 of Keras, which is an AI language library used for AI programming.

The AI model is generated through evaluation of the learned AI model (operation S130) (operation S140). The evaluation of the learned AI model (operation S130) is performed by using the test data. Throughout the present disclosure, the 'learned AI model' means learning the learning data and deciding the learned model after testing through the test data even without special mention. Hereinafter, the AI model for learning the fabric identifying method will be described.

The artificial intelligence (AI) is one field of computer science and information technology that studies methods to make computers mimic intelligent human behaviors such as reasoning, learning, self-improving and the like.

In addition, the artificial intelligence does not exist on its own, but is rather directly or indirectly related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed.

More specifically, machine learning is a technology that investigates and builds systems, and algorithms for such systems, which are capable of learning, making predictions, and enhancing their own performance on the basis of experiential data. Machine learning algorithms, rather than only executing rigidly set static program commands, may take an approach that builds models for deriving predictions and decisions from inputted data.

Many Machine Learning algorithms have been developed on how to classify data in the Machine Learning. Representative examples of such machine learning algorithms for data classification include a decision tree, a Bayesian network, a support vector machine (operation SVM), an artificial neural network (ANN), and so forth.

Decision tree refers to an analysis method that uses a tree-like graph or model of decision rules to perform classification and prediction.

Bayesian network may include a model that represents the probabilistic relationship (conditional independence) among a set of variables. Bayesian network may be appropriate for data mining via unsupervised learning.

SVM may include a supervised learning model for pattern detection and data analysis, heavily used in classification and regression analysis.

ANN is a data processing system modelled after the mechanism of biological neurons and interneuron connections, in which a number of neurons, referred to as nodes or processing elements, are interconnected in layers.

ANNs are models used in machine learning and may include statistical learning algorithms conceived from biological neural networks (particularly of the brain in the central nervous system of an animal) in machine learning and cognitive science.

ANNs may refer generally to models that have artificial neurons (nodes) forming a network through synaptic interconnections, and acquires problem-solving capability as the strengths of synaptic interconnections are adjusted throughout training.

The terms 'artificial neural network' and 'neural network' may be used interchangeably herein.

An ANN may include a number of layers, each including a number of neurons. In addition, the Artificial Neural Network may include the synapse for connecting between neuron and neuron.

An ANN may be defined by the following three factors: (1) a connection pattern between neurons on different layers; (2) a learning process that updates synaptic weights; and (3) an activation function generating an output value from a weighted sum of inputs received from a lower layer.

The Artificial Neural Network may include network models of the method such as Deep Neural Network (DNN), Recurrent Neural Network (RNN), Bidirectional Recurrent Deep Neural Network (BRDNN), Multilayer Perceptron (MLP), and Convolutional Neural Network (CNN), but is not limited thereto.

The terms "layer" and "hierarchy" may be used interchangeably herein.

An ANN may be classified as a single-layer neural network or a multi-layer neural network, based on the number of layers therein.

In general, a single-layer neural network may include an input layer and an output layer.

In addition, a general Multi-Layer Neural Network is composed of an Input layer, one or more Hidden layers, and an Output layer.

The Input layer is a layer that accepts external data, the number of neurons in the Input layer is equal to the number of input variables, and the Hidden layer is disposed between the Input layer and the Output layer and receives a signal from the Input layer to extract the characteristics to transfer it to the Output layer. The output layer receives a signal from the hidden layer and outputs an output value based on the received signal. The Input signal between neurons is multiplied by each connection strength (weight) and then summed, and if the sum is larger than the threshold of the neuron, the neuron is activated to output the output value obtained through the activation function.

Meanwhile, the Deep Neural Network including a plurality of Hidden layers between the Input layer and the Output layer may be a representative Artificial Neural Network that implements Deep Learning, which is a type of Machine Learning technology.

The Artificial Neural Network may be trained by using training data. Here, the training may refer to the process of determining parameters of the artificial neural network by using the training data, to perform tasks such as classification, regression analysis, and clustering of inputted data. Such parameters of the artificial neural network may include synaptic weights and biases applied to neurons.

An artificial neural network trained using training data may classify or cluster inputted data according to a pattern within the inputted data.

Throughout the present specification, an artificial neural network trained using training data may be referred to as a trained model.

Hereinbelow, learning paradigms of an artificial neural network will be described in detail.

The learning method of the Artificial Neural Network may be largely classified into Supervised Learning, Unsupervised Learning, Semi-supervised Learning, and Reinforcement Learning.

The Supervised Learning is a method of the Machine Learning for inferring one function from the training data.

Then, among the thus inferred functions, outputting consecutive values is referred to as regression, and predicting and outputting a class of an input vector is referred to as classification.

In the Supervised Learning, the Artificial Neural Network is learned in a state where a label for the training data has been given.

Here, the label may refer to a target answer (or a result value) to be guessed by the artificial neural network when the training data is inputted to the artificial neural network.

Throughout the present specification, the target answer (or a result value) to be guessed by the artificial neural network when the training data is inputted may be referred to as a label or labeling data.

Throughout the present specification, assigning one or more labels to training data in order to train an artificial neural network may be referred to as labeling the training data with labeling data.

Training data and labels corresponding to the training data together may form a single training set, and as such, they may be inputted to an artificial neural network as a training set.

The training data may exhibit a number of features, and the training data being labeled with the labels may be interpreted as the features exhibited by the training data being labeled with the labels. In this case, the training data may represent a feature of an input object as a vector.

Using training data and labeling data together, the artificial neural network may derive a correlation function between the training data and the labeling data. Then, the parameter of the Artificial Neural Network may be determined (optimized) by evaluating the function inferred from the Artificial Neural Network.

Unsupervised learning is a machine learning method that learns from training data that has not been given a label.

More specifically, unsupervised learning may be a training scheme that trains an artificial neural network to discover a pattern within given training data and perform classification by using the discovered pattern, rather than by using a correlation between given training data and labels corresponding to the given training data.

Examples of unsupervised learning include, but are not limited to, clustering and independent component analysis.

Examples of artificial neural networks using unsupervised learning include, but are not limited to, a generative adversarial network (GAN) and an autoencoder (AE).

GAN is a machine learning method in which two different artificial intelligences, a generator and a discriminator, improve performance through competing with each other.

The generator may be a model generating new data that generates new data based on true data.

The discriminator may be a model recognizing patterns in data that determines whether inputted data is from the true data or from the new data generated by the generator.

Furthermore, the generator may receive and learn from data that has failed to fool the discriminator, while the discriminator may receive and learn from data that has succeeded in fooling the discriminator. Accordingly, the generator may evolve so as to fool the discriminator as effectively as possible, while the discriminator evolves so as to distinguish, as effectively as possible, between the true data and the data generated by the generator.

An auto-encoder (AE) is a neural network which aims to reconstruct its input as output.

More specifically, AE may include an input layer, at least one hidden layer, and an output layer.

Since the number of nodes in the hidden layer is smaller than the number of nodes in the input layer, the dimensionality of data is reduced, thus leading to data compression or encoding.

Furthermore, the data outputted from the hidden layer may be inputted to the output layer. Given that the number of nodes in the output layer is greater than the number of nodes in the hidden layer, the dimensionality of the data increases, thus leading to data decompression or decoding.

Furthermore, in the AE, the inputted data is represented as hidden layer data as interneuron connection strengths are adjusted through training. The fact that when representing information, the hidden layer is able to reconstruct the inputted data as output by using fewer neurons than the input layer may indicate that the hidden layer has discovered a hidden pattern in the inputted data and is using the discovered hidden pattern to represent the information.

Semi-supervised learning is machine learning method that makes use of both labeled training data and unlabeled training data.

One of semi-supervised learning techniques involves guessing the label of unlabeled training data, and then using this guessed label for learning. This technique may be used advantageously when the cost associated with the labeling process is high.

Reinforcement learning may be based on a theory that given the condition under which a reinforcement learning agent may determine what action to choose at each time instance, the agent may find an optimal path to a solution solely based on experience without reference to data.

The Reinforcement Learning may be mainly performed by a Markov Decision Process (MDP).

Markov decision process consists of four stages: first, an agent is given a condition containing information required for performing a next action; second, how the agent behaves in the condition is defined; third, which actions the agent should choose to get rewards and which actions to choose to get penalties are defined; and fourth, the agent iterates until future reward is maximized, thereby deriving an optimal policy.

An artificial neural network is characterized by features of its model, the features including an activation function, a loss function or cost function, a learning algorithm, an optimization algorithm, and so forth. Also, the hyperparameters are set before learning, and model parameters may be set through learning to specify the architecture of the artificial neural network.

For instance, the structure of an artificial neural network may be determined by a number of factors, including the number of hidden layers, the number of hidden nodes included in each hidden layer, input feature vectors, target feature vectors, and so forth.

Hyperparameters may include various parameters which need to be initially set for learning, much like the initial values of model parameters. Also, the model parameters may include various parameters sought to be determined through learning.

For instance, the hyperparameters may include initial values of weights and biases between nodes, mini-batch size, iteration number, learning rate, and so forth. Furthermore, the model parameters may include a weight between nodes, a bias between nodes, and so forth.

Loss function may be used as an index (reference) in determining an optimal model parameter during the learning process of an artificial neural network. Learning in the artificial neural network involves a process of adjusting model parameters so as to reduce the loss function, and the purpose of learning may be to determine the model parameters that minimize the loss function.

Loss functions typically use means squared error (MSE) or cross entropy error (CEE), but the present disclosure is not limited thereto.

Cross-entropy error may be used when a true label is one-hot encoded. One-hot encoding may include an encoding method in which among given neurons, only those corresponding to a target answer are given 1 as a true label value, while those neurons that do not correspond to the target answer are given 0 as a true label value.

In machine learning or deep learning, learning optimization algorithms may be deployed to minimize a cost function, and examples of such learning optimization algorithms include gradient descent (GD), stochastic gradient descent (operation SGD), momentum, Nesterov accelerate gradient (NAG), Adagrad, AdaDelta, RMSProp, Adam, and Nadam.

GD includes a method that adjusts model parameters in a direction that decreases the output of a cost function by using a current slope of the cost function.

The direction in which the model parameters are to be adjusted may be referred to as a step direction, and a size by which the model parameters are to be adjusted may be referred to as a step size.

Here, the step size may mean a learning rate.

GD obtains a slope of the cost function through use of partial differential equations, using each of model parameters, and updates the model parameters by adjusting the model parameters by a learning rate in the direction of the slope.

SGD may include a method that separates the training dataset into mini batches, and by performing gradient descent for each of these mini batches, increases the frequency of gradient descent.

Adagrad, AdaDelta and RMSProp may include methods that increase optimization accuracy in SGD by adjusting the step size, and may also include methods that increase optimization accuracy in SGD by adjusting the momentum and step direction. Adam may include a method that combines momentum and RMSProp and increases optimization accuracy in SGD by adjusting the step size and step direction. Nadam may include a method that combines NAG and RMSProp and increases optimization accuracy by adjusting the step size and step direction.

Learning rate and accuracy of an artificial neural network rely not only on the structure and learning optimization algorithms of the artificial neural network but also on the hyperparameters thereof. Accordingly, in order to obtain a good learning model, it is important to choose a proper structure and learning algorithms for the artificial neural network, but also to choose proper hyperparameters.

In general, the artificial neural network is first trained by experimentally setting hyperparameters to various values, and based on the results of training, the hyperparameters may be set to optimal values that provide a stable learning rate and accuracy.

The learning of the AI model for identifying the type of the fabric may be performed in any one form among supervised learning, unsupervised learning, and reinforcement learning.

Convolutional Neural Network (CNN) is the most representative method of the deep neural network, which characterizes images from small features to complex ones. The CNN is an artificial neural network that is composed of one or several convolutional layers and general artificial neural network layers mounted on it to perform preprocessing on the convolutional layer. For example, in order to learn the image of a human face through the CNN, the first step is to extract simple features by using a filter to create a convolutional layer, and to add a new layer, for example, a pooling layer for extracting more complex feature from these features. The convolutional layer is a layer for extracting features through a convolutional operation, and performs multiplication with a regular pattern. The pooling layer reduces the dimension of the image through sub-sampling with a layer for abstracting an input space. For example, it may compress a facial image of a 28×28 size into 12×12 by creating a 24×24 feature map, respectively, by using four filters for one person and performing sub-sampling (or pooling) by a stride. In the next layer, it may create 12 feature maps in 8×8 size, perform sub-sampling by 4×4 again, and finally classify the image by learning with the neural network with the input of 12×34×4=192. Accordingly, multiple convolutional layers may be connected to extract the features of the image and finally learned by using an error back propagation neural network. The advantage of the CNN is to create a filter itself for characterizing the features of the image through artificial neural network learning.

In an embodiment of the present disclosure, the CNN artificial neural network model may have a deep neural network structure having an image on a structure of one fabric as an input layer, five hidden layers, and five output layers of cotton, hemp, wool, silk, and synthetic fibers.

In another embodiment of the present disclosure, the CNN artificial neural network model may have a deep neural network structure having an input layer of a fabric structure, at least two among a color, a pattern, a button, a sleeve contour, a leg contour, or a neck contour of the clothing, five hidden layers, and five output layers of cotton, hemp, wool, silk, and synthetic fibers.

Figure 8:
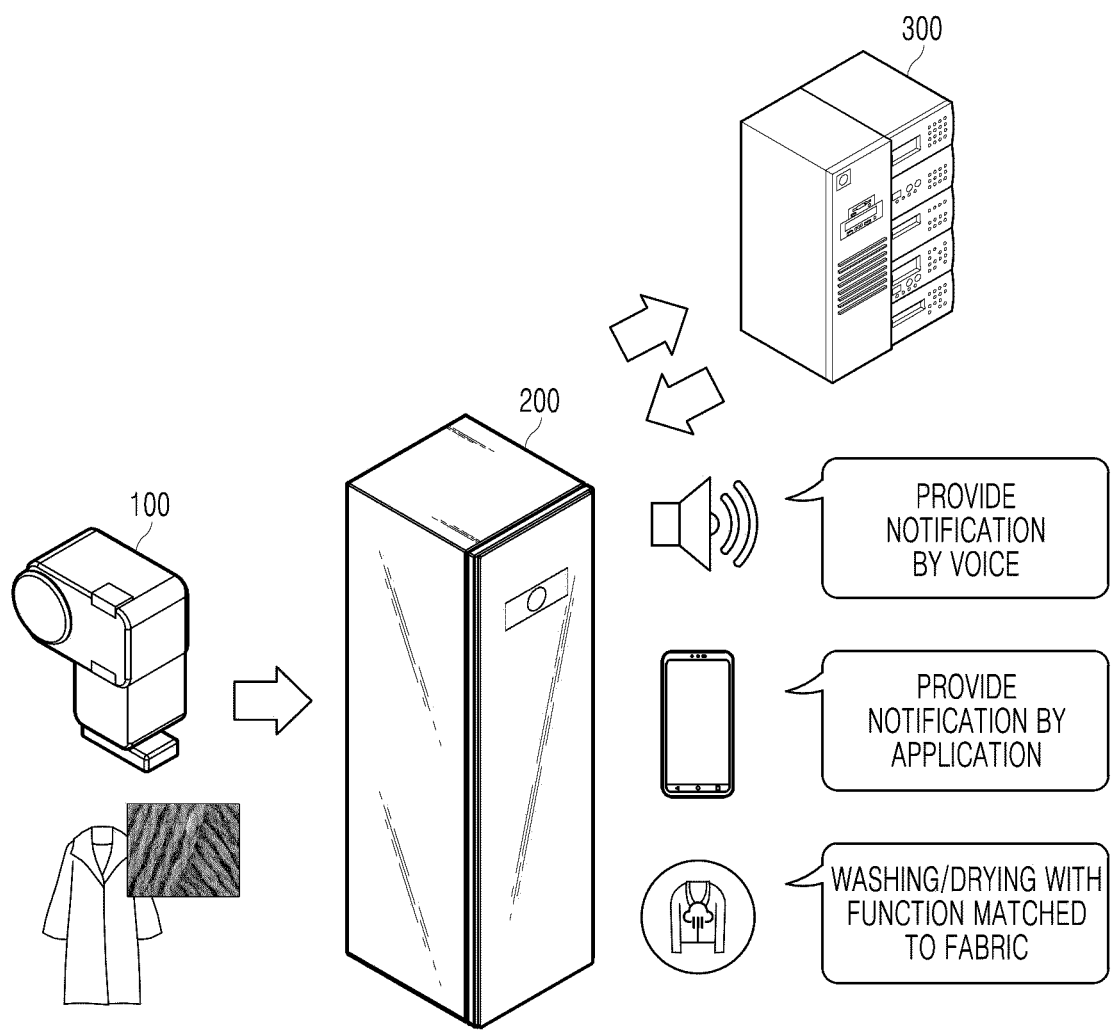
FIG. 8 is an exemplary diagram notifying a user of fabric type information identified through the fabric identifying apparatus according to an embodiment of the present disclosure.

FIG. 8 is an exemplary diagram for notifying a user of the fabric type information identified through the fabric identifying apparatus according to an embodiment of the present disclosure.

When the information on the type of the fabric is first received in the interlocked clothing-related home appliance 200 from the fabric identifying apparatus 100, the data storage device or the cloud server 300 of the interlocked clothing-related home appliance 200 may i) store the fabric information when there is no record of the received fabric information. The clothing-related home appliance 200 may provide a notification function and a washing/drying function as a function suitable for the fabric through a voice or an application with the information on the type of the fabric. The following is an example of the notification function.

(Example of Notification)
1) Start washing a wool course.
2) Washing with this function may damage the fabric of the silk!
3) At the same time, clothing that should not be washed/dried are mixed.

The data storage device or the cloud server 300 of the interlocked clothing-related home appliance 200 may ii) confirm the previous history and execute a function on the corresponding fabric information if there is already a record of the received fabric information. The received fabric information may update usage information in the data storage device or the cloud server. The updated information may be used later as big data.

Embodiments according to the present disclosure described above may be implemented in the form of a computer program that may be executed through various components on a computer, and such a computer program may be recorded in a computer readable medium. At this time, the media may be magnetic media such as a hard disk, a floppy disk, and a magnetic tape, optical recording media such as a CD-ROM and a DVD, magneto-optical media such as a floptical disk, and hardware devices specifically configured to store and execute program instructions, such as a ROM, a RAM, and a flash memory.

Meanwhile, the computer program may be specially designed and configured for the present disclosure, or may be known and available to those skilled in the computer software field. Examples of computer programs may include not only machine code generated by a compiler, but also high-level language code that may be executed by a computer using an interpreter, etc.

In the specification (particularly in the claims) of the present disclosure, the use of the term "above" and the similar indicating term may be used in the singular and the plural. In addition, in the present disclosure, when the range is described, it includes the disclosure to which the individual values belonging to the range are applied (unless stated to the contrary), and each individual value constituting the range is the same as described in the detailed description of the disclosure.

Operations constituting the method of the present disclosure may be performed in appropriate order unless explicitly described in terms of order or described to the contrary. The present disclosure is not necessarily limited to the order of operations given in the description. All examples described herein or the terms indicative thereof ("for example," etc.) used herein are merely to describe the present disclosure in greater detail. Accordingly, it should be understood that the scope of the present disclosure is not limited to the example embodiments described above or by the use of such terms unless limited by the appended claims. Accordingly, it should be understood that the scope of the present disclosure is not limited to the example embodiments described above or by the use of such terms unless limited by the appended claims. Also, it should be apparent to those skilled in the art that various alterations, substitutions, and modifications may be made within the scope of the appended claims or equivalents thereof.

Accordingly, technical ideas of the present disclosure are not limited to the above-mentioned embodiments, and it is intended that not only the appended claims, but also all changes equivalent to claims, should be considered to fall within the scope of the present disclosure.

What is claimed is:

1. A method for identifying a fabric of a clothing, comprising:
   obtaining image information including a fabric structure of the clothing;
   applying data on the fabric structure included in the image information to a learned artificial intelligence model trained to identify one or more types of fabrics;
   identifying a type of fabric of the clothing through the learned artificial intelligence model;
   outputting information on the type of fabric from the learned artificial intelligence model;
   transmitting information on the identified type of fabric to a clothing-related home appliance;
   searching whether a type of fabric matching the obtained image information is present in a non-transitory memory;
   after outputting the information on the type of fabric from the learned artificial intelligence model, storing, in the non-transitory memory, the identified type of fabric that matches the obtained image information;
   based on a determination that a type of fabric matching the obtained image information is not present in the non-transitory memory, perform operations comprising:
      applying the obtained image information to the learned artificial intelligence model,
      outputting the information on the type of fabric from the learned artificial intelligence model,
      identifying a type of fabric of the clothing through the learned artificial intelligence model,
      storing the identified type of fabric matching the obtained image information in the non-transitory memory, and
      transmitting the information on the identified type of fabric to the clothing-related home appliance; and
   based on a determination that the type of fabric matching the obtained image information is present in the non-transitory memory, transmitting the information on the type of fabric identified from the non-transitory memory to the clothing-related home appliance.

2. The method of claim 1, wherein the learned artificial intelligence model comprises a fabric type identifying engine configured to identify and output the type of fabric of the clothing, the fabric type identifying engine being trained with learning data comprising fabric data of a plurality of fabric structures and label data obtained by matching the fabric data to labels of the type of fabric.

3. The method of claim 2, wherein obtaining the image information comprises obtaining an image of a tag part of the clothing, and
   wherein the label data are obtained based on recognizing one or more characters from the image of the tag part.

4. The method of claim 2, wherein the fabric type identifying engine is trained to identify the type of fabric through a Convolution Neural Network (CNN) with image data corresponding to the obtained image information.

5. The method of claim 1, wherein obtaining the image information comprises obtaining an image of a part of the clothing, and
wherein the learned artificial intelligence model comprises a fabric type identifying engine configured to identify and output the type of fabric, the fabric type identifying engine being trained with learning data comprising (i) at least one of a color, a pattern, or a contour of the part of the clothing, or data on the fabric structure of the part of the clothing, and (ii) label data obtained by matching the data on the fabric structure included in the image information to a label of the type of fabric.

6. The method of claim 1, further comprising:
obtaining waveform information from the clothing by a millimeter wave (mmWave) sensor,
wherein identifying the type of fabric comprises identifying the type of fabric through the learned artificial intelligence model based on the data on the fabric structure and the waveform information from the clothing.

7. The method of claim 1, further comprising:
obtaining information of a near infrared wave from the clothing by a near infrared (NIR) spectrometer,
wherein identifying the type of fabric comprises identifying the type of fabric through the learned artificial intelligence model based on the data on the fabric structure and the information of the near infrared wave from the clothing.

8. The method of claim 1, wherein obtaining the image information comprises obtaining the image information through a camera of a mobile terminal, the mobile terminal comprising a fabric identifying application program,
wherein applying the data on the fabric structure to the learned artificial intelligence model and outputting the information on the type of fabric from the learned artificial intelligence model are performed through the fabric identifying application, and
wherein transmitting the information on the identified type of fabric to the clothing-related home appliance is performed through a communication module of the mobile terminal.

9. A non-transitory computer readable recording medium having stored thereon a computer program which, when executed by at least one processor, causes performance of computer-executable instructions comprising:
obtaining image information including a fabric structure of a clothing;
applying data on the fabric structure included in the image information to a learned artificial intelligence model;
identifying a type of fabric of the clothing through the learned artificial intelligence model;
outputting the information on the type of fabric from the learned artificial intelligence model;
transmitting the information on the identified type of fabric to a clothing-related home appliance;
searching whether a type of fabric matching the obtained image information is present in a non-transitory memory;
after outputting the information on the type of fabric from the learned artificial intelligence model, storing, in the non-transitory memory, the identified type of fabric that matches the obtained image information;
based on a determination that a type of fabric matching the obtained image information is not present in the non-transitory memory, perform operations comprising:

applying the obtained image information to the learned artificial intelligence model,
outputting the information on the type of fabric from the learned artificial intelligence model,
identifying a type of fabric of the clothing through the learned artificial intelligence model,
storing the identified type of fabric matching the obtained image information in the non-transitory memory, and
transmitting the information on the identified type of fabric to the clothing-related home appliance; and
based on a determination that the type of fabric matching the obtained image information is present in the non-transitory memory, transmitting the information on the type of fabric identified from the non-transitory memory to the clothing-related home appliance.

10. A fabric identifying apparatus, comprising:
a camera configured to obtain image information including a fabric structure of a clothing;
a fabric identifier configured to identify and output a type of fabric of the clothing through a learned artificial intelligence model based on data on the fabric structure included in the image information;
a communicator configured to transmit information on the identified type of fabric to a clothing-related home appliance; and
a non-transitory memory configured to store the identified type of fabric that matches the obtained image information,
wherein the fabric identifier is configured to determine and output the type of fabric of the clothing by:
searching whether a type of fabric matching the obtained image information is present in the non-transitory memory, and
based on a type of fabric matching the obtained image information is not present in the non-transitory memory, identifying and outputting a type of fabric of the clothing matching the obtained image information through the learned artificial intelligence model.

11. The fabric identifying apparatus of claim 10, wherein the learned artificial intelligence model comprises a fabric type identifying engine configured to identify and output the type of fabric of the clothing, the fabric type identifying engine being trained with learning data comprising fabric data on a plurality fabric structures and label data obtained by matching the fabric data to labels of the type of fabric.

12. The fabric identifying apparatus of claim 11, wherein the camera is configured to obtain an image of a tag part of the clothing, and
wherein the label data are obtained based on recognizing one or more characters in the image of the tag part.

13. The fabric identifying apparatus of claim 11, wherein the fabric type identifying engine is trained to identify the type of fabric through a Convolution Neural Network (CNN) with image data corresponding to the obtained image information.

14. The fabric identifying apparatus of claim 10, wherein the camera is configured to obtain an image of a part of the clothing, and
wherein the learned artificial intelligence model comprises a fabric type identifying engine configured to identify and output the type of fabric of the clothing, the fabric type identifying engine being trained with learning data comprising (i) at least one of a color, a pattern, or a contour of the part of the clothing, or data on fabric structures of the part of the clothing, and (ii)

label data obtained by matching the data on the fabric structure included in the image information to a label of the type of fabric.

15. The fabric identifying apparatus of claim 10, further comprising:
a millimeter wave (mmWave) sensor configured to obtain waveform information from the clothing,
wherein the fabric identifier is configured to identify and output the type of fabric through the learned artificial intelligence model based on the data on the fabric structure included in the image information and the waveform information from the clothing.

16. The fabric identifying apparatus of claim 10, further comprising:
a near infrared (NIR) spectrometer configured to obtain information of a near infrared wave from the clothing,
wherein the fabric identifier is configured to identify and output the type of fabric through the learned artificial intelligence model based on the data on the fabric structure included in the image information and the information of the near infrared wave from the clothing.

17. The fabric identifying apparatus of claim 10, wherein the fabric identifier comprises:
a data collector configured to collect fabric data on a plurality of fabric structures from the camera;
an artificial intelligence model learner configured to train a fabric type identifying engine to identify and output the type of fabric of the clothing with learning data comprising the fabric data and label data obtained by matching the fabric data to labels of the type of fabric; and
a fabric type classifier configured to identify and output the type of fabric of the clothing through the fabric type identifying engine based on the fabric data from the camera.

18. A fabric identifying system comprising:
a fabric identifying apparatus configured to identify a type of fabric of a clothing; and
a server configured to communicate with the fabric identifying apparatus,
wherein the fabric identifying apparatus comprises:
a camera configured to obtain image information including a fabric structure of the clothing,
a fabric identifier configured to identify and output the type of fabric based on the fabric structure included in the image information,
a communicator configured to transmit the image information on the fabric structure of the clothing to the server, and
a non-transitory memory configured to store the identified type of fabric that matches the obtained image information,
wherein the server comprises an artificial intelligence model learner configured to generate a learned fabric type identifying engine by training, through a deep neural network, an artificial intelligence model with the image information on the fabric structure of the clothing received from the fabric identifying apparatus,
wherein the server is configured to transmit the learned fabric type identifying engine to the fabric identifying apparatus,
wherein the fabric identifier is configured to identify the type of fabric of the clothing through the learned fabric type identifying engine received from the server,
wherein the communicator is configured to transmit the information on the type of fabric identified by the fabric identifier to a clothing-related home appliance, and
wherein the fabric identifier is configured to determine and output the type of fabric of the clothing by:
searching whether a type of fabric matching the obtained image information is present in the non-transitory memory, and
based on a type of fabric matching the obtained image information is not present in the non-transitory memory, identifying and outputting a type of fabric of the clothing matching the obtained image information through the learned fabric type identifying engine received from the server.

* * * * *